United States Patent
Qiu et al.

(10) Patent No.: US 10,211,362 B2
(45) Date of Patent: Feb. 19, 2019

(54) DISPLAY PANEL AND METHOD OF MANUFACTURING THE SAME, DISPLAY DEVICE AND WEARABLE INTELLIGENT DEVICE

(71) Applicants: BOE Technology Group Co., Ltd., Beijing (CN); Ordos Yuansheng Optoelectronics Co., Ltd., Ordos, Inner Mongolia (CN)

(72) Inventors: Yun Qiu, Beijing (CN); Jiuxia Yang, Beijing (CN)

(73) Assignees: BOE TECHNOLOGY GROUP CO., LTD., Beijing (CN); ORDOS YUANSHENG OPTOELECTRONICS CO., LTD., Ordos, Inner Mongolia (CN)

( * ) Notice: Subject to any disclaimer, the term of this patent is extended or adjusted under 35 U.S.C. 154(b) by 151 days.

(21) Appl. No.: 15/095,673

(22) Filed: Apr. 11, 2016

(65) Prior Publication Data

US 2017/0042426 A1 Feb. 16, 2017

(30) Foreign Application Priority Data

Aug. 11, 2015 (CN) .......................... 2015 1 0491020

(51) Int. Cl.
*H01L 33/00* (2010.01)
*A61B 5/00* (2006.01)
(Continued)

(52) U.S. Cl.
CPC ........ *H01L 33/005* (2013.01); *A61B 5/02427* (2013.01); *A61B 5/02438* (2013.01);
(Continued)

(58) Field of Classification Search
CPC ............... H01L 33/005; A61B 5/02427; A61B 5/02438; A61B 5/681; A61B 5/742
(Continued)

(56) References Cited

U.S. PATENT DOCUMENTS

| 5,766,234 A | * | 6/1998 | Chen | ................ | A61B 17/00234 |
| | | | | | 600/373 |
| 6,289,238 B1 | * | 9/2001 | Besson | .............. | A61B 5/14552 |
| | | | | | 128/903 |

(Continued)

FOREIGN PATENT DOCUMENTS

| CN | 1816228 A | 8/2006 |
| CN | 1816231 A | 8/2006 |

(Continued)

OTHER PUBLICATIONS

First Chinese Office Action, for Chinese Patent Application No. 201510491020.8, dated May 2, 2017, 22 pages.

(Continued)

*Primary Examiner* — Christopher A Flory
(74) *Attorney, Agent, or Firm* — Kinney & Lange, P.A.

(57) ABSTRACT

A display panel and a method of manufacturing the same, a display device and a wearable intelligent device are disclosed. The display panel includes: a substrate; a display unit arranged on the substrate; a monitoring light emitting unit formed on a side of the substrate away from the display unit, for emitting monitoring light toward an object in a direction facing away from the display unit; and a light receiving unit formed on the side of the substrate away from the display unit, for receiving reflected monitoring light from the object and generating monitoring data of the object based to the reflected monitoring light. With technique solutions of the invention, devices for monitoring a user's body conditions can be integrated on the back of the substrate, that is, be (Continued)

integrated with the substrate, such that the display panel has a more compact structure and a more aesthetic appearance.

12 Claims, 5 Drawing Sheets

(51) Int. Cl.
 *A61B 5/024*  (2006.01)
 *G01J 3/42*  (2006.01)
 *H01L 31/173*  (2006.01)
 *H01L 31/18*  (2006.01)
 *G01J 3/10*  (2006.01)
 *G01J 3/02*  (2006.01)

(52) U.S. Cl.
 CPC .............. *A61B 5/681* (2013.01); *A61B 5/742* (2013.01); *G01J 3/0259* (2013.01); *G01J 3/10* (2013.01); *G01J 3/42* (2013.01); *H01L 31/173* (2013.01); *H01L 31/18* (2013.01); *A61B 2560/0468* (2013.01); *A61B 2562/0233* (2013.01); *A61B 2562/164* (2013.01); *H01L 2933/005* (2013.01); *H01L 2933/0016* (2013.01)

(58) Field of Classification Search
 USPC ......................................................... 600/479
 See application file for complete search history.

(56) References Cited

U.S. PATENT DOCUMENTS

| | | | | | |
|---|---|---|---|---|---|
| 7,828,473 | B2* | 11/2010 | Tanaka | ................ | G02B 6/0056 362/612 |
| 7,919,342 | B2* | 4/2011 | Cok | .................... | H05B 33/145 257/79 |
| 7,923,918 | B2* | 4/2011 | Tamaki | ................. | C09K 11/02 313/501 |
| 9,122,349 | B1* | 9/2015 | Chang | ................... | G09G 3/3413 |
| 9,791,471 | B2* | 10/2017 | Qiu | ..................... | G01P 15/0802 |
| 2002/0165439 | A1* | 11/2002 | Schmitt | ............... | A61B 5/0059 600/309 |
| 2002/0186209 | A1* | 12/2002 | Cok | ........................ | G06F 3/041 345/173 |
| 2003/0109030 | A1* | 6/2003 | Uchida | .............. | A61B 5/14532 435/287.1 |
| 2003/0225322 | A1* | 12/2003 | Uchiyama | .......... | A61B 5/14525 600/323 |
| 2004/0075382 | A1* | 4/2004 | Stegamat | ........... | H01L 51/5234 313/506 |
| 2004/0075637 | A1* | 4/2004 | Izumi | ............... | H01L 27/14678 345/104 |
| 2004/0252867 | A1* | 12/2004 | Lan | ..................... | G06K 9/0004 382/124 |
| 2005/0140265 | A1* | 6/2005 | Hirakata | ............. | H01L 51/5259 313/483 |
| 2007/0029560 | A1* | 2/2007 | Su | .......................... | H01L 33/02 257/98 |
| 2007/0100218 | A1* | 5/2007 | Sweitzer | .............. | A61B 5/0002 600/323 |
| 2007/0100219 | A1* | 5/2007 | Sweitzer | .............. | A61B 5/0002 600/323 |
| 2007/0123756 | A1* | 5/2007 | Kitajima | ............ | A61B 5/14552 600/300 |
| 2008/0082004 | A1* | 4/2008 | Banet | ................. | A61B 5/02028 600/485 |
| 2008/0097172 | A1* | 4/2008 | Sawada | ................ | A61B 5/0261 600/310 |
| 2008/0105875 | A1* | 5/2008 | Maekawa | ............ | G03F 7/70791 257/72 |
| 2008/0154101 | A1* | 6/2008 | Jain | ..................... | A61B 5/0017 600/309 |
| 2008/0218068 | A1* | 9/2008 | Cok | ..................... | H05B 33/145 313/505 |
| 2008/0239458 | A1* | 10/2008 | Sachs | ................. | G02B 27/1026 359/294 |
| 2008/0248191 | A1* | 10/2008 | Daniels | ................... | B82Y 20/00 427/66 |
| 2009/0068918 | A1* | 3/2009 | Cok | ..................... | H05B 33/145 445/49 |
| 2009/0105563 | A1* | 4/2009 | Yajima | ............... | A61B 5/15134 600/309 |
| 2009/0131774 | A1* | 5/2009 | Sweitzer | ............. | A61B 5/0002 600/323 |
| 2009/0292335 | A1* | 11/2009 | Leonov | .................... | A61N 1/08 607/35 |
| 2010/0198026 | A1* | 8/2010 | Young | .................. | A61B 5/0059 600/306 |
| 2011/0288421 | A1* | 11/2011 | Banet | ................. | A61B 5/02028 600/485 |
| 2012/0150047 | A1* | 6/2012 | Terumoto | ........... | A61B 5/02427 600/479 |
| 2012/0157804 | A1* | 6/2012 | Rogers | ................. | A61B 5/0422 600/345 |
| 2012/0165759 | A1* | 6/2012 | Rogers | ................. | A61B 5/6867 604/264 |
| 2013/0046163 | A1* | 2/2013 | Sweitzer | ............. | A61B 5/0002 600/340 |
| 2013/0128333 | A1* | 5/2013 | Agrawal | ................. | G02F 1/157 359/273 |
| 2013/0135546 | A1* | 5/2013 | Wang | ................... | H01L 33/0041 349/33 |
| 2013/0137994 | A1* | 5/2013 | Sawada | ................ | A61B 5/0261 600/479 |
| 2013/0252024 | A1* | 9/2013 | Okada | ..................... | C07F 5/022 428/704 |
| 2013/0285035 | A1* | 10/2013 | Taka | ...................... | C09K 11/06 257/40 |
| 2014/0042897 | A1* | 2/2014 | Kamada | ................. | H01L 33/54 313/502 |
| 2014/0077236 | A1* | 3/2014 | Yamada | .............. | H01L 25/0753 257/88 |
| 2014/0092597 | A1* | 4/2014 | Kamada | ............. | F21V 23/002 362/249.01 |
| 2014/0183342 | A1* | 7/2014 | Shedletsky | ........... | G06F 1/1637 250/215 |
| 2014/0184987 | A1* | 7/2014 | Kusuura | ............ | G02F 1/133602 349/67 |
| 2014/0350366 | A1* | 11/2014 | Akiyama | ............... | H01L 27/288 600/328 |
| 2015/0003040 | A1* | 1/2015 | Bessho | ..................... | F21V 9/40 362/84 |
| 2015/0060780 | A1* | 3/2015 | Hsu | ..................... | H01L 51/0097 257/40 |
| 2015/0208933 | A1* | 7/2015 | Satomi | ............... | A61B 5/02416 600/479 |
| 2015/0228869 | A1* | 8/2015 | Yoo | ........................ | H01L 33/54 362/97.3 |
| 2015/0265182 | A1* | 9/2015 | Jain | ...................... | A61B 5/0017 600/302 |
| 2016/0070131 | A1* | 3/2016 | Kimura | ................. | G02F 1/13454 349/38 |
| 2016/0197250 | A1* | 7/2016 | Yamada | .............. | H01L 25/0753 257/88 |
| 2016/0218156 | A1* | 7/2016 | Shedletsky | ........... | G06F 1/1637 |
| 2017/0078513 | A1* | 3/2017 | Chang | ................... | G06F 3/0488 |
| 2017/0214004 | A1* | 7/2017 | Shedletsky | ........... | G06F 1/1637 |
| 2017/0250326 | A1* | 8/2017 | Kamada | .................. | H01L 33/56 |
| 2017/0256687 | A1* | 9/2017 | Yoo | ........................ | H01L 33/54 |
| 2017/0270342 | A1* | 9/2017 | He | ......................... | G06F 3/0412 |

FOREIGN PATENT DOCUMENTS

| | | |
|---|---|---|
| CN | 101330865 A | 12/2008 |
| CN | 101460088 A | 6/2009 |
| CN | 101505657 A | 8/2009 |
| CN | 102413761 A | 4/2012 |
| CN | 102576164 A | 7/2012 |

(56) References Cited

FOREIGN PATENT DOCUMENTS

| | | |
|---|---|---|
| CN | 203456513 U | 2/2014 |
| CN | 104706334 A | 6/2015 |
| JP | 1987127072 A | 6/1987 |
| WO | 2014197243 A2 | 12/2014 |

OTHER PUBLICATIONS

Second Chinese Office Action, for Chinese Patent Application No. 201510491020.8, dated Jan. 11, 2018.

\* cited by examiner

US 10,211,362 B2

DISPLAY PANEL AND METHOD OF MANUFACTURING THE SAME, DISPLAY DEVICE AND WEARABLE INTELLIGENT DEVICE

CROSS-REFERENCE TO RELATED APPLICATION

This application claims the benefit of the Chinese Patent Application No. 201510491020.8 filed on Aug. 11, 2015 in the State Intellectual Property Office of China, the whole disclosure of which is incorporated herein by reference.

BACKGROUND OF THE INVENTION

Field of the Invention

Embodiments of the present disclosure generally relate to the field of display technologies, and particularly, to a display panel, a display device, a wearable intelligent device and a method of manufacturing a display panel.

Description of the Related Art

With development and application of wearable intelligent devices, a health monitoring function of an intelligent terminal has attracted more and more attention from the people. In most of current intelligent terminals including a health monitoring unit, such as a smart wristband, a smart watch, a smart phone or the like, the monitoring unit is designed as a separate structure, and even when the health monitoring unit is provided on the display device, elements associated with health monitoring unit are generally designed independent of the display panel, which results in disadvantages such as low integration, incompact arrangement and the like.

SUMMARY

An object of the present disclosure is to improve integrity of a monitoring device on an intelligent terminal.

According to an aspect of the present disclosure, there is provided a display panel, comprising:

a substrate;

a display unit arranged on the substrate;

a monitoring light emitting unit formed on the substrate and located on a side of the substrate away from the display unit, and configured to emit monitoring light toward an object in a direction facing away from the display unit; and a light receiving unit formed on the substrate and located on the side of the substrate away from the display unit, and configured to receive reflected monitoring light from the object and to generate monitoring data of the object based on the reflected monitoring light.

Preferably, the monitoring light emitting unit comprises a light emitting layer made of an electroluminescent material and/or a photoluminescence material.

Preferably, when the light emitting layer is made of an electroluminescent material, the monitoring light emitting unit further comprises:

a first electrode layer formed on the side of the substrate away from the display unit, the light emitting layer being formed on a side of the first electrode layer away from the substrate; and a second electrode layer formed on a side of the light emitting layer away from the first electrode.

Preferably, the light emitting layer is formed of a monochromatic electroluminescent material.

Preferably, the light receiving unit comprises a photoelectric sensor.

Preferably, the light receiving unit comprises:

a third electrode layer formed on the side of the substrate away from the display unit;

a first type semiconductor layer formed on a side of the third electrode layer away from the substrate;

a depletion layer formed on a side of the first type semiconductor layer away from the third electrode layer;

a second type semiconductor layer formed on a side of the depletion layer away from the first type semiconductor layer; and a fourth electrode layer formed on a side of the second type semiconductor layer away from the depletion layer, wherein the first type semiconductor layer is formed of one of an N-type semiconductor material and a P-type semiconductor material, and the second type semiconductor layer is formed of the other of the N-type semiconductor material and the P-type semiconductor material.

Preferably, the above display panel further comprises an isolation layer formed on the side of the substrate away from the display unit and located between the substrate and the monitoring light emitting unit and the light receiving unit.

Preferably, the above display panel further comprises a protection layer formed on the monitoring light emitting unit and the light receiving unit, for covering the monitoring light emitting unit and the light receiving unit.

According to another aspect of the present disclosure, there is provided a display device, comprising the display panel as described above.

According to a further aspect of the present disclosure, there is provided a wearable intelligent device, comprising the above display device.

According to a still further aspect of the present disclosure, there is provided a method of manufacturing the above display panel, comprising steps of:

forming the monitoring light emitting unit on the substrate, the monitoring light emitting unit being located on a side of the substrate away from the display unit and configured to emit monitoring light toward an object in a direction facing away from the display unit; and forming the light receiving unit on the substrate, the light receiving unit being located on the side of the substrate away from the display unit and configured to receive reflected monitoring light from the object and to generate monitoring data of the object according to the reflected monitoring light.

Preferably, the step of forming the monitoring light emitting unit comprises:

forming a first electrode layer on the substrate, the first electrode layer being located on the side of the substrate away from the display unit;

forming a light emitting layer on a side of the first electrode layer away from the substrate; and forming a second electrode layer on a side of the light emitting layer away from the first electrode.

Preferably, the step of forming the light receiving unit comprises:

forming a third electrode layer on the substrate, the third electrode layer being located on the side of the substrate away from the display unit;

forming a first type semiconductor layer on a side of the third electrode layer away from the substrate;

forming a depletion layer on a side of the first type semiconductor layer away from the third electrode layer;

forming a second type semiconductor layer on a side of the depletion layer away from the first type semiconductor layer; and forming a fourth electrode layer on a side of the second type semiconductor layer away from the depletion layer, wherein the first type semiconductor layer is formed of one of an N-type semiconductor material and a P-type semiconductor material, and the second type semiconductor layer is formed of the other one of the N-type semiconductor material and the P-type semiconductor material.

Preferably, the third electrode layer and the first electrode layer are formed at the same time, and/or the fourth electrode layer and the second electrode layer are formed at the same time.

Preferably, before forming the monitoring light emitting unit and the light receiving unit, the method further comprises a step of:

forming an isolation layer on the side of substrate away from the display unit, thereby the step of forming the monitoring light emitting unit comprises:

forming the monitoring light emitting unit on a side of the isolation layer away from substrate;

and the step of forming the light receiving unit comprises:

forming the light receiving unit on the side of the isolation layer away from substrate.

Preferably, the method further comprises a step of forming a protection layer over the monitoring light emitting unit and the light receiving unit.

With the above technique solutions, devices capable of monitoring a user's body conditions can be integrated on the back of the substrate of the display panel, that is, be integrated with the substrate, such that the display panel has a more compact structure and a more aesthetic appearance.

BRIEF DESCRIPTION OF THE DRAWINGS

Features and advantages of the present invention will become more apparent when referring to the accompanying drawings, which are schematic and should not be interpreted as being limitative to the present invention, and in which.

Figure 1:
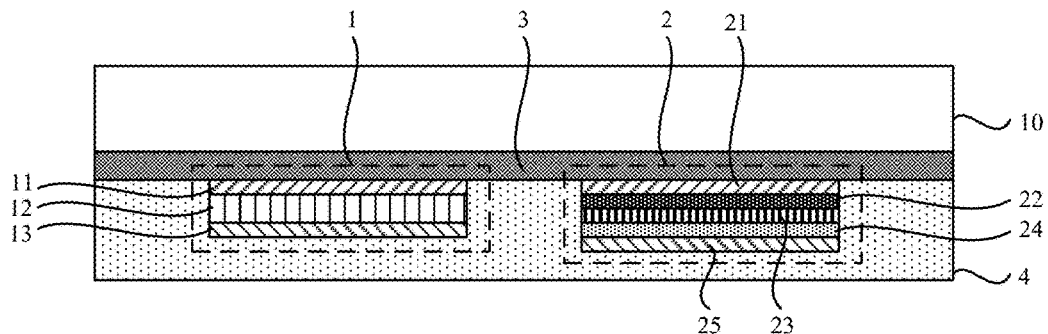
FIG. 1 is a structural schematic diagram showing a display panel according to an embodiment of the present disclosure.

EXPLANATION OF REFERENCE NUMERALS 1-monitoring light emitting unit; 11-first electrode layer; 12-light emitting layer; 13-second electrode layer; 2-light receiving unit; 21-second electrode layer; 22-first type semiconductor layer; 23-depletion layer; 24-second type semiconductor layer; 25-fourth electrode layer; 3-isolation layer; 4-protection layer; 10-substrate.

DETAINED DESCRIPTION OF PREFERRED EMBODIMENTS OF THE INVENTION

In order to make clearer understanding of the above objects, features and advantages of the present disclosure, the present invention will be described hereinafter in detail with reference to exemplary embodiments and attached drawings. It is noted that in case of no conflict, the embodiments and features thereof of the present disclosure may be randomly combined.

In the following detailed description, for purposes of explanation, numerous specific details are set forth in order to provide a thorough understanding of the disclosed embodiments. It will be apparent, however, the present invention may be embodied in many different forms and should not be construed as being limited to the embodiments set forth herein; rather, these embodiments are provided so that the present invention will be thorough and complete, and will fully convey the concept of the disclosure to those skilled in the art.

A display panel according to an embodiment of the present disclosure, as shown in FIG. 1, comprises a substrate 10 and a display unit (not shown) arranged on the substrate 10. In an example, the display unit may comprise structures such as a thin film transistor, a pixel and the like. The display panel further comprises:

a monitoring light emitting unit 1 formed on the substrate 10 and located on a side of the substrate away from the display unit (a lower side of the substrate 10 in FIG. 1, that is, a back side of the substrate), and configured to emit monitoring light toward an object such as human body in a direction facing away from the display unit; and a light receiving unit 2 formed on the substrate 10 and located on the side of the substrate 10 away from the display unit, and configured to receive reflected monitoring light from the object and to generate monitoring data of the object based the reflected monitoring light, for example, generate monitoring data indicative of human body health or body conditions.

According to embodiments of the present disclosure, the monitoring light emitting unit 1 and the light receiving unit 2 may be integrated on the back (the side of the substrate away from display unit) of the substrate 10 of the display panel, that is, be integrated with the substrate 10, such that the display panel has a more compact structure and a more aesthetic appearance.

When a user wears a wearable intelligent device that is manufactured to include the display panel, his/her body health may be monitored through the monitoring light emitting unit 1 and the light receiving unit 2 of the device.

For example, the monitoring light emitting unit 1 and the light receiving unit 2 may be controlled by inputting instructions to software; the monitoring light emitting unit 1 and the light receiving unit 2 may be also controlled through a physical or virtual button, or through a voice mode.

The monitoring light emitting unit 1 and the light receiving unit 2 may enter a health monitoring state upon receiving a start-up function instruction from a system, then the monitoring light emitting unit 1 emits monitoring light towards human body and the light receiving unit 2 receives reflected light in real time.

Preferably, the monitoring light emitting unit 1 comprises a light emitting layer 12 made of an electroluminescent material and/ or a photoluminescence material.

The monitoring light emitting unit 1 may emit monitoring light through the electroluminescent material and/ or photoluminescence material. When the light emitting layer 11 of the monitoring light emitting unit 1 is made of electroluminescent material, electrical excitation is provided to the light emitting layer 11 by applying an electric filed to electrodes 11 and 13 on either side of the light emitting layer 11, such that the light emitting layer 11 emits light for monitoring; when the light emitting layer 11 of the monitoring light emitting unit 1 is made of photoluminescence material, a light excitation unit may be designed to excite the photoluminescence material to emit light for monitoring. Thus, monitoring may be done under many conditions, and applicability is better.

Preferably, when the light emitting layer 12 is made of an electroluminescent material, the monitoring light emitting unit 1 further comprises:

a first electrode layer 11 formed on the side of the substrate 10 away from the display unit, the light emitting layer 12 being formed on a side of the first electrode layer 11 away from the substrate 10; and a second electrode layer 13 formed on a side of the light emitting layer 12 away from the first electrode 11.

When the display panel is supplied with electrical power, the first electrode layer 11 and the second electrode layer 13 will be applied with voltages to excite the light emitting layer to emit light for monitoring.

Preferably, the light emitting layer 12 is made of monochromatic electroluminescent material.

In an example, the light emitting layer 12 is a monochromatic light source, which is more stable and will not emit unstable light due to external interference, so that a more accurate monitoring effect may be obtained.

Preferably, light receiving unit 12 comprises a photoelectric sensor.

The monitoring light emitting unit 11 emits monitoring light, which is incident onto the human body as incident light for monitoring health of the human body.

In an example, blood in blood vessels of a user will vary as his/her heart rate changes (for example, a flow rate of the blood will increase when the heart rate increases). As reflection characteristic of light incident onto the skin will vary as the blood varies, the light receiving unit 12 may receive the light reflected by the skin and convert light signal into an electrical signal, and then a value of the heart rate may be calculated based on change in the electrical signal, thereby obtaining data regarding a change of physical condition of the user.

Preferably, the light receiving unit 2 may comprises a photodiode. Exemplarily, the photodiode comprises:

a third electrode layer 21 formed on the side of the substrate 10 away from the display unit;

a first type semiconductor layer 22 formed on a side of the third electrode layer 21 away from the substrate 10;

a depletion layer 23 formed on a side of the first type semiconductor layer 22 away from the third electrode layer 21;

a second type semiconductor layer 24 formed on a side of the depletion layer 23 away from the first type semiconductor layer 22; and a fourth electrode layer 25 formed on a side of the second type semiconductor layer 24 away from the depletion layer 23.

In an example, the first type semiconductor layer 22 is formed of one of an N-type semiconductor material and a P-type semiconductor material, while the second type semiconductor layer 24 is formed of the other of the N-type semiconductor material and the P-type semiconductor material.

It is noted that the first type semiconductor layer 22 may be formed on a side of the depletion layer 23 adjacent to the substrate 10, or the second type semiconductor layer 24 may be formed on the side of the depletion layer 23 adjacent to the substrate 10. For example, relative positions of the semiconductor layers may be arranged according to voltages supplied to the third electrode layer 21 and the fourth electrode layer 25.

Preferably, the display panel according to embodiments of the present disclosure may further comprise an isolation layer 3 formed on the side of the substrate 10 away from the display unit, wherein the monitoring light emitting unit 1 and the light receiving unit 2 are formed on a side of the isolation layer 3 away from the substrate 10.

The isolation layer 3 is provided to prevent external moisture from entering the monitoring light emitting unit 1 or the light receiving unit 2, so that the monitoring light emitting unit 1 may normally emit light, and the light receiving unit 2 can normally convert the light signal into the electrical signal.

Preferably, the display panel according to embodiments of the present disclosure may further comprise a protection layer 4 formed over the monitoring light emitting unit 1 and the light receiving unit 2, for covering and packaging the monitoring light emitting unit 1 and the light receiving unit 2.

The protection layer 4, on one hand, may package the monitoring light emitting unit 1 and the light receiving unit 2 so that the back of the display panel is flat and aesthetic, and on the other hand, may prevent the monitoring light emitting unit 1 and the light receiving unit 2 from being damaged from the outside.

Embodiments of the present disclosure further provide a display device, comprising the display panel as described above.

It is noted that the display device according to the embodiments of the present disclosure may be an electronic paper, a mobile phone, a tablet computer, a TV set, a notebook PC, a digital picture frame, a navigator or any other product or component having a display function.

Embodiments of the present disclosure further provide a wearable intelligent device, comprising the display device as described above. For example, the wearable intelligent device may be a smart watch, a smart wristband or the like.

Figure 2:
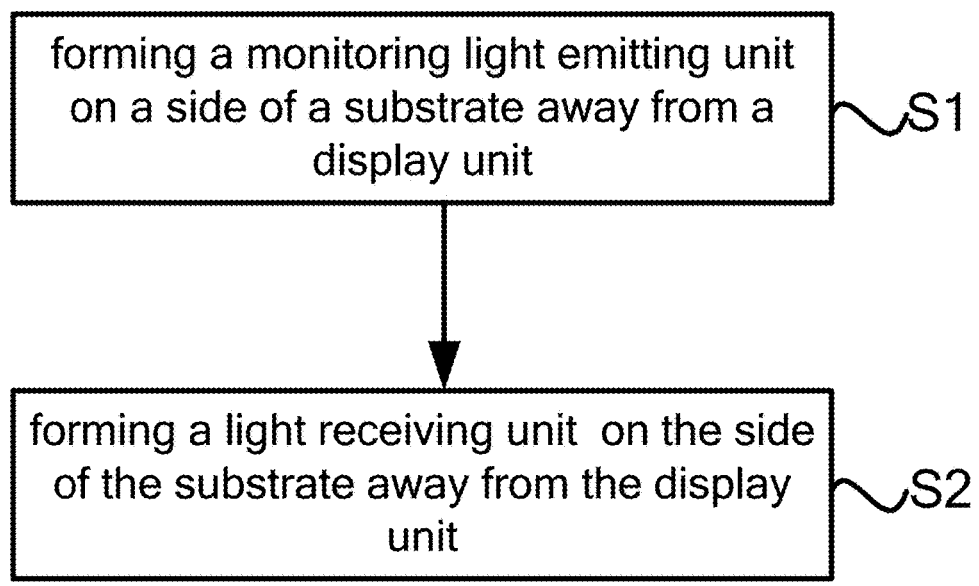
FIG. 2 is a schematic flowchart showing a method of manufacturing a display panel according to an embodiment of the present disclosure.

Embodiments of the present disclosure further provide a method of manufacturing the above display panel, as shown in FIG. 2, comprising following steps of:

S1 of forming the monitoring light emitting unit 1 on the substrate 10, the monitoring light emitting unit 1 being located on the side of the substrate 10 away from the display unit and configured to emit monitoring light toward an object in a direction facing away from the display unit; and S2 of forming the light receiving unit 2 on the substrate 10, the light receiving unit 2 being located on the side of the substrate 10 away from the display unit and configured to receive reflected monitoring light from the object and to generate monitoring data of the object according to the reflected monitoring light.

It is noted that in the above method, structures such as the display unit may be firstly formed on one side of the substrate 10, then the monitoring light emitting unit 1 and the light receiving unit 2 are formed on an opposite side of the substrate 10; alternatively, the monitoring light emitting unit 1 and the light receiving unit 2 may be firstly formed on one side of the substrate 10, and then structures such as the display unit are formed on an opposite side of the substrate 10. In embodiments of the present disclosure, sequence of forming the monitoring light emitting unit 1 and the light receiving unit 2 is not limited to any particular order.

Figure 3:
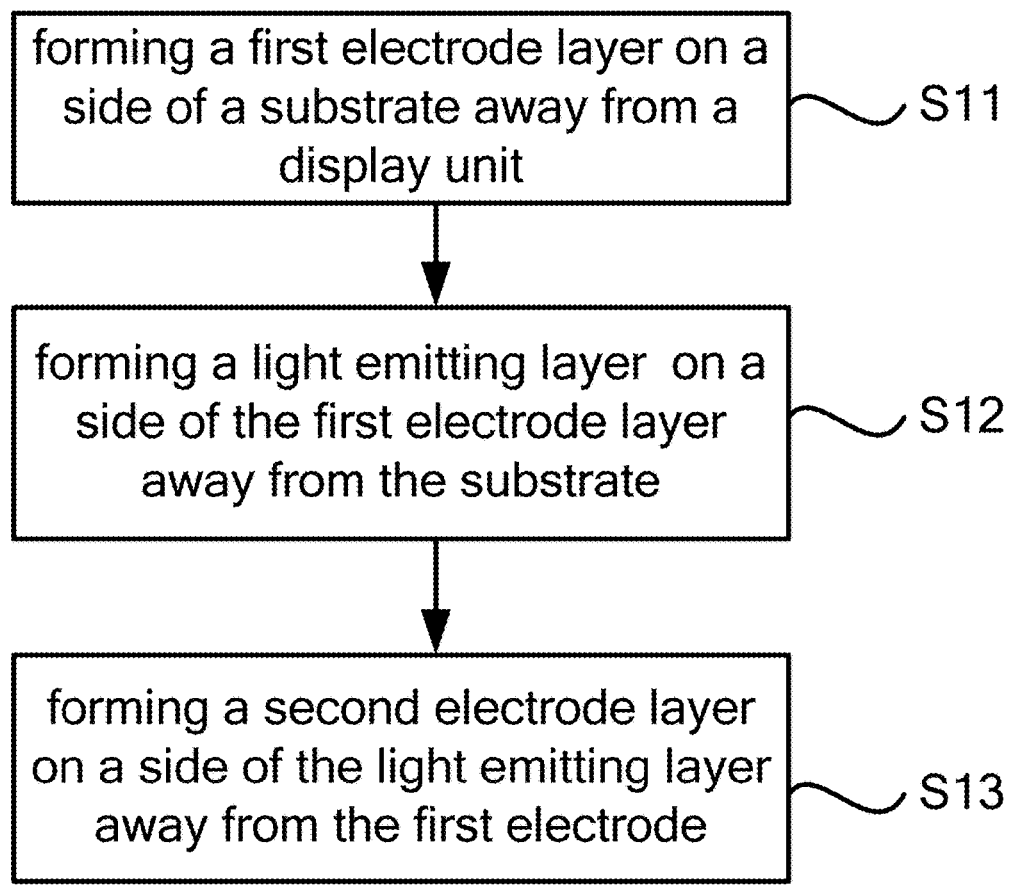
FIG. 3 is a schematic flowchart showing a method of manufacturing a monitoring light emitting unit according to an embodiment of the present disclosure.
Figure 6:
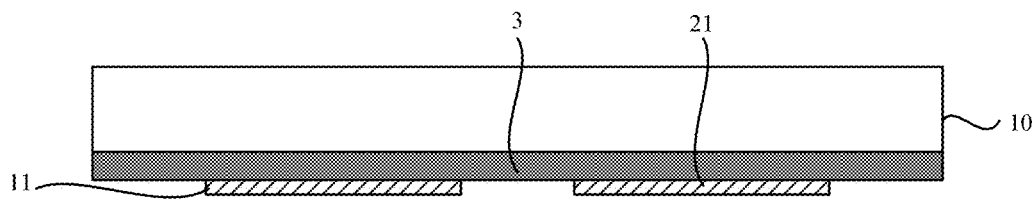
Figure 7:
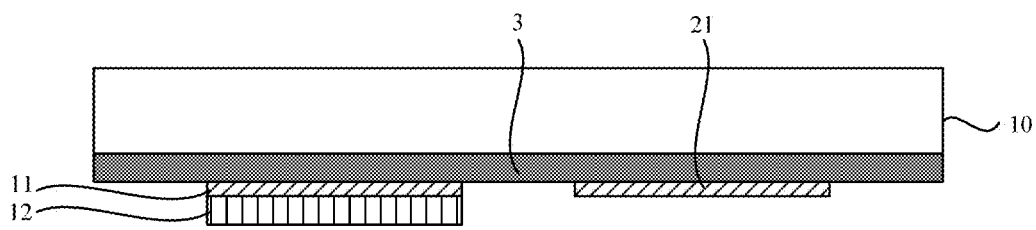
Figure 11:
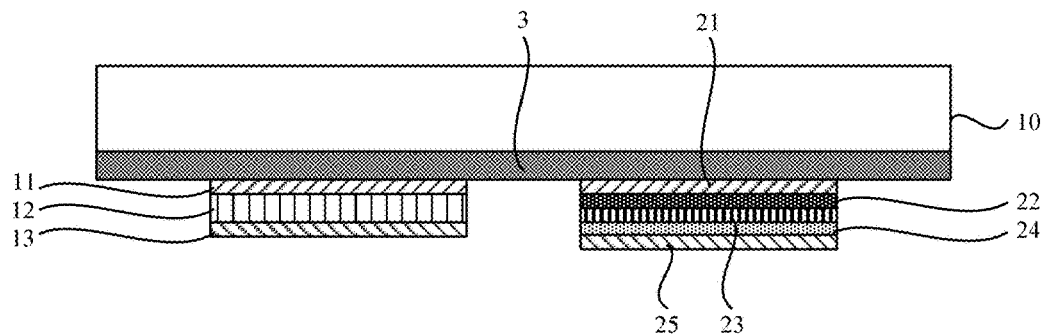

As shown in FIG. 3, preferably, the step of forming the monitoring light emitting unit 1 comprises steps of:

S11 of forming a first electrode layer 11 on the substrate 10, as shown in FIG. 6;

S12 of forming a light emitting layer 12 on a side of the first electrode layer 11 away from the substrate 10, as shown in FIG. 7, for example, the light emitting layer 12 may be formed through ink jetting, printing or coating process and a curing process; and S13 of forming a second electrode layer 13 on a side of the light emitting layer 12 away from the first electrode, as shown in FIG. 11.

Figure 4:
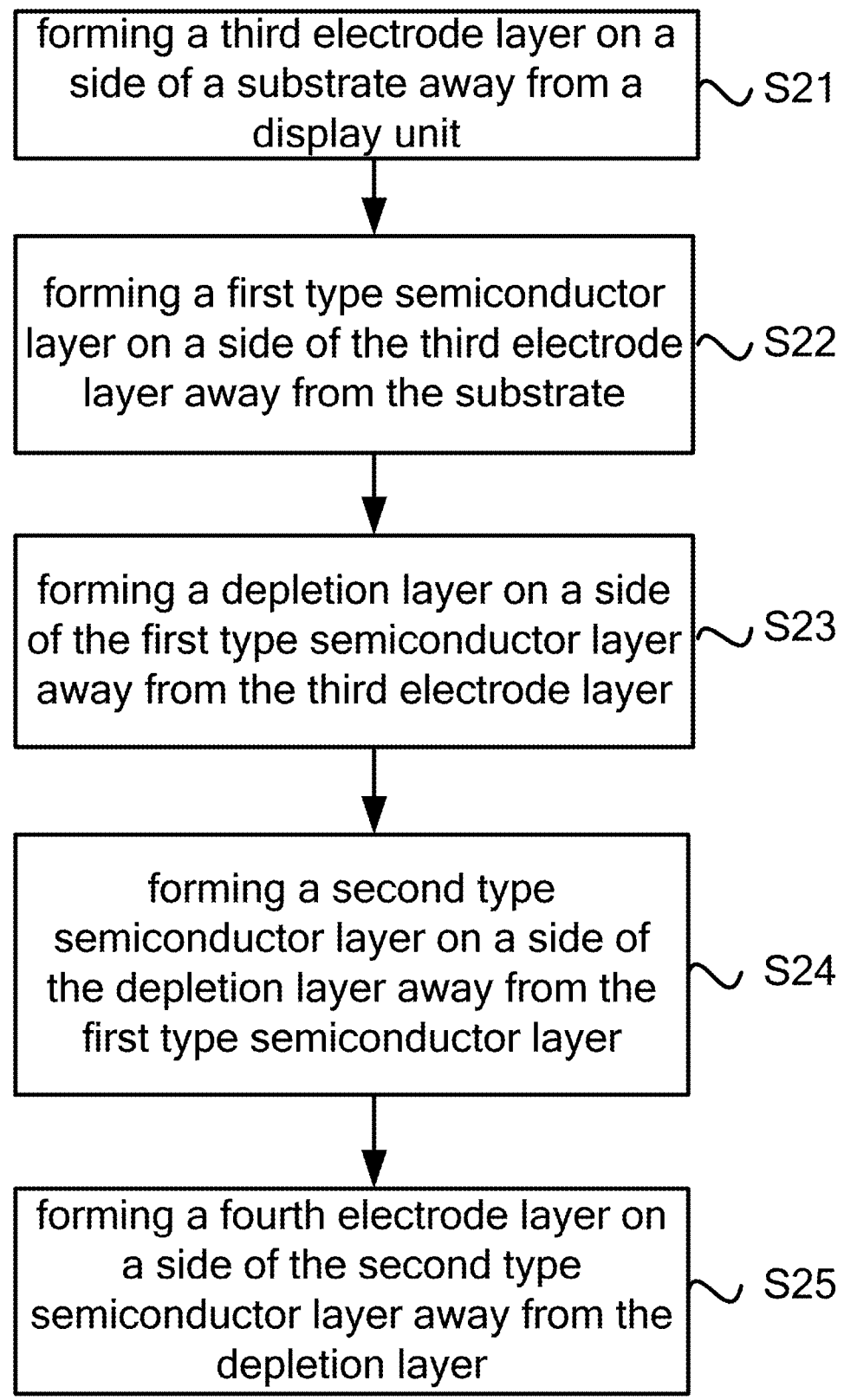
FIG. 4 is a schematic flowchart showing a method of manufacturing a light receiving unit according to an embodiment of the present disclosure.
Figure 8:
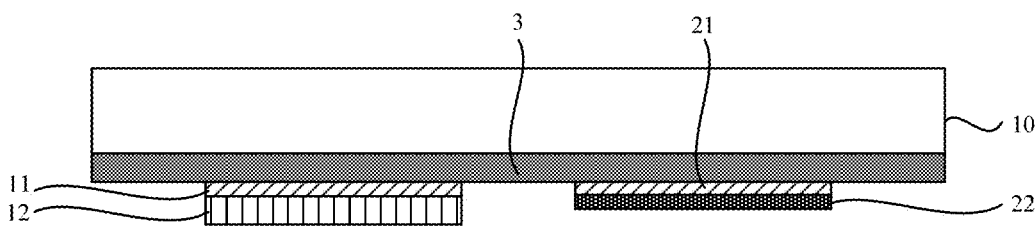
Figure 9:
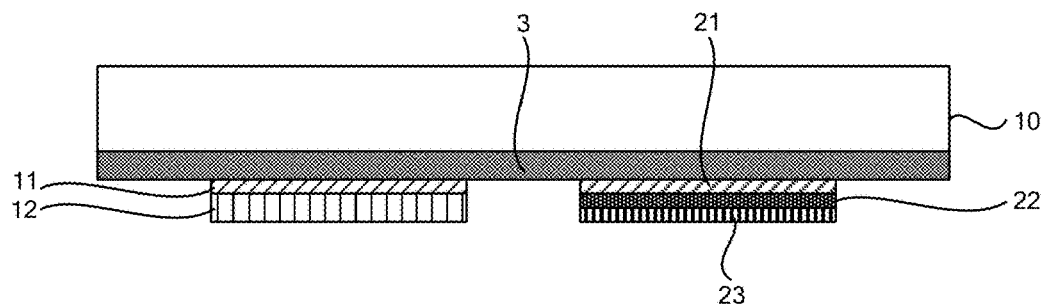
Figure 10:
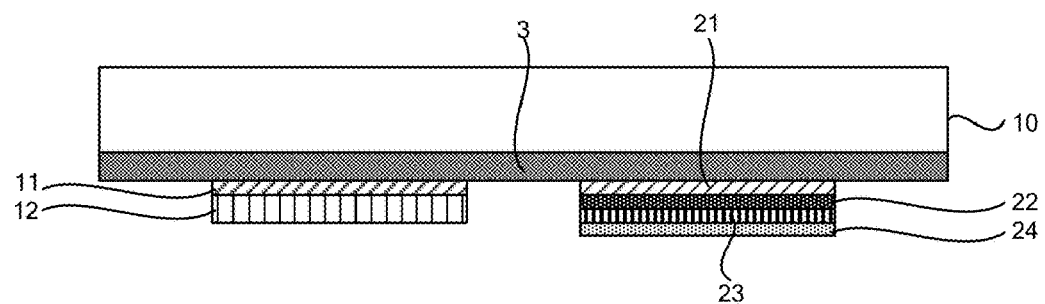

As shown in FIG. 4, preferably, the step of forming the light receiving unit 2 comprises steps of:

S21 of forming a third electrode layer 21 on the side of the substrate 10 away from the display unit, as shown in FIG. 7;

S22 of forming a first type semiconductor layer 22 on a side of the third electrode layer 21 away from the substrate 10, as shown in FIG. 8;

S23 of forming a depletion layer 23 on a side of the first type semiconductor layer 22 away from the third electrode layer 21, as shown in FIG. 9;

S24 of forming a second type semiconductor layer 24 on a side of the depletion layer 23 away from the first type semiconductor layer 22, as shown in FIG. 10; and S25 of forming a fourth electrode layer 25 on a side of the second type semiconductor layer 24 away from the depletion layer 23, as shown in FIG. 11.

For example, the first type semiconductor layer, the depletion layer and the second type semiconductor layer of the photodiode may be manufactured respectively through a PECVD (Plasma Enhanced Chemical Vapor Deposition) process.

Preferably, the third electrode layer 21 is formed while forming the first electrode layer 11, and the fourth electrode layer 25 is formed while forming the second electrode layer 13; for example, respective electrode layers may be manufactured through coating and curing processes.

Figure 5:
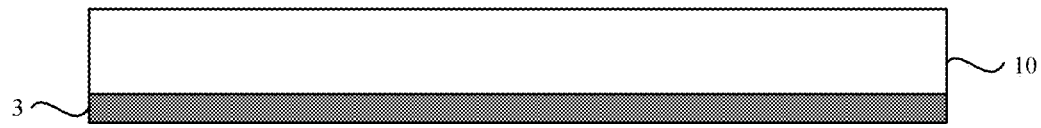
FIG. 5 to FIG. 12 are schematic diagrams showing steps of a method of manufacturing a display panel according to an embodiment of the present disclosure.

As shown in FIG. 5, preferably, before forming the monitoring light emitting unit and the light receiving unit, the method may further comprise a step of:

S0 of forming an isolation layer 3 on the side of substrate 10 away from the display unit. For example, the isolation layer may be manufactured through a PECVD process.

In this instance, the step of forming the monitoring light emitting unit 1 comprises forming the monitoring light emitting unit 1 on a side of the isolation layer 3 away from substrate 10, and the step of forming the light receiving unit 2 comprises forming the light receiving unit 2 on the side of the isolation layer 3 away from substrate 10.

Figure 12:
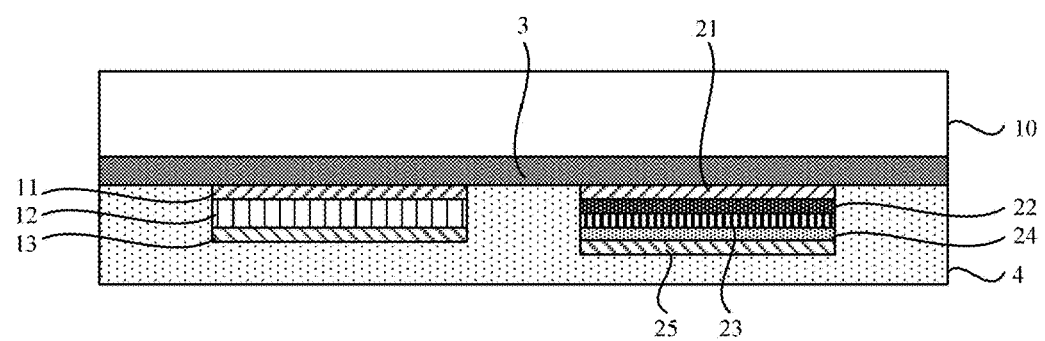

As shown in FIG. 12, preferably, the above method may further comprise step of:

S4 of forming a protection layer 4 over the monitoring light emitting unit 1 and the light receiving unit 2. For example, the protection layer may be manufactured through a PECVD process.

In an example, manufacturing processes used in the above steps may include, for example, film formation processes such as deposition process, sputtering process and the like, and patterning processes such as etching process and the like.

Technique solutions of the present disclosure have been described above in detail in conjunction with the drawings. Compared with the wearable intelligent device for monitoring health of the user in prior art whose components are incompact in arrangement, the display panel according to embodiments of the present invention may have a more compact structure and a more aesthetic appearance by integrating devices capable of monitoring a user' physical conditions on the back of the substrate of the display panel, that is, be integrated with the substrate.

It is noted in the drawings, sizes of layers and regions may be magnified for clear illustration. Further, it will be understood that when it is described that an element or layer is "on" another element or layer, it may be directly on another element or layer, or there may be an intermediate element or layer therebetween. Similarly, it will also be understood that when it is described that an element or layer is "under" another element or layer, it may be directly under another element or layer, or there may be one or more intermediate element or layer therebetween. In addition, it will be appreciated that when it is described that a layer or element is "between" two layers or elements, it may be the only one layer or element between the two layers or elements, or there may be more than one or more intermediate element or layer. Similar reference numerals indicate similar elements throughout the document.

In the present disclosure, terms "first", "second", "third" and the like are only intended for description purpose, but could not be understood as indicating or implying relative importance. Term "a plurality of" refers to two or more, unless otherwise expressly defined.

The above described contents are only preferred embodiments of the present disclosure, and are not intended to limit the present disclosure. Various modification and changes may be made to the present disclosure by those skilled in the art. All changes, alternatives or modifications which are made within the principles and spirit of the present disclosure should fall within the scopes of the present invention.

What is claimed is:

1. A display panel, comprising:
    a substrate;
    a display unit arranged on the substrate;
    a monitoring light emitting unit formed on the substrate and located on a side of the substrate facing away from the display unit, and configured to emit monitoring light toward an object in a direction facing away from the display unit;
    a light receiving unit formed on the substrate and located on the side of the substrate facing away from the display unit, and configured to receive reflected monitoring light from the object and to generate monitoring data of the object based on the reflected monitoring light;
    an isolation layer formed on the side of the substrate facing away from the display unit and located between the substrate and the monitoring light emitting unit and the light receiving unit; and
    a single protection layer formed over the monitoring light emitting unit and the light receiving unit to package the monitoring light emitting unit and the light receiving unit such that in a cross sectional view of the display panel, each of the monitoring light emitting unit and the light receiving unit is surrounded by the singe protection layer at three sides thereof, the single protection layer being in contact with the isolation layer,
    wherein the monitoring light emitting unit and the light receiving unit are formed on a side of the isolation layer facing away from the substrate, such that external moisture is prevented by the isolation layer from entering the monitoring light emitting unit and the light receiving unit.

2. The display panel according to claim 1, wherein the monitoring light emitting unit comprises:
    a light emitting layer made of an electroluminescent material and/or a photoluminescence material.

3. The display panel according to claim 2, wherein the light emitting layer is made of an electroluminescent material, and the monitoring light emitting unit further comprises:
   a first electrode layer formed on the side of the substrate away from the display unit, the light emitting layer being formed on a side of the first electrode layer away from the substrate; and
   a second electrode layer formed on a side of the light emitting layer away from the first electrode.

4. The display panel according to claim 3, wherein the light emitting layer is formed of a monochromatic electroluminescent material.

5. The display panel according to claim 1, wherein the light receiving unit comprises a photoelectric sensor.

6. The display panel according to claim 5, wherein the light receiving unit comprises:
   a third electrode layer formed on the side of the substrate away from the display unit;
   a first type semiconductor layer formed on a side of the third electrode layer away from the substrate;
   a depletion layer formed on a side of the first type semiconductor layer away from the third electrode layer;
   a second type semiconductor layer formed on a side of the depletion layer away from the first type semiconductor layer; and
   a fourth electrode layer formed on a side of the second type semiconductor layer away from the depletion layer,
   wherein the first type semiconductor layer is formed of one of an N-type semiconductor material and a P-type semiconductor material, and the second type semiconductor layer is formed of the other one of the N-type semiconductor material and the P-type semiconductor material.

7. A display device, comprising the display panel according to claim 1.

8. A wearable intelligent device, comprising the display device according to claim 7.

9. A method of manufacturing the display panel according to claim 1, comprising steps of:
   forming the isolation layer on the side of the substrate facing away from the display unit;
   forming the monitoring light emitting unit on a side of the isolation layer facing away from the substrate such that the isolation layer is located between the substrate and the monitoring light emitting unit, the monitoring light emitting unit being located on the side of the substrate away from the display unit and configured to emit monitoring light toward an object in the direction facing away from the display unit;
   forming the light receiving unit on the side of the isolation layer facing away from the substrate such that the isolation layer is located between the substrate and the light receiving unit, the light receiving unit being located on the side of the substrate away from the display unit and configured to receive reflected monitoring light from the object and to generate monitoring data of the object based on the reflected monitoring light; and
   forming the single protection layer over the monitoring light emitting unit and the light receiving unit to package the monitoring light emitting unit and the light receiving unit such that in a cross sectional view of the display panel, each of the monitoring light emitting unit and the light receiving unit is surrounded by the single protection layer at three sides thereof, the single protection layer being in contact with the isolation layer.

10. The method according to claim 9, wherein the step of forming the monitoring light emitting unit comprises:
    forming a first electrode layer on the substrate, the first electrode layer being located on the side of the substrate away from the display unit;
    forming a light emitting layer on a side of the first electrode layer away from the substrate; and
    forming a second electrode layer on a side of the light emitting layer away from the first electrode.

11. The method according to claim 10, wherein the step of forming the light receiving unit comprises:
    forming a third electrode layer on the substrate, the third electrode layer being located on the side of the substrate away from the display unit;
    forming a first type semiconductor layer on a side of the third electrode layer away from the substrate;
    forming a depletion layer on a side of the first type semiconductor layer away from the third electrode layer;
    forming a second type semiconductor layer on a side of the depletion layer away from the first type semiconductor layer; and
    forming a fourth electrode layer on a side of the second type semiconductor layer away from the depletion layer,
    wherein the first type semiconductor layer is formed of one of an N-type semiconductor material and a P-type semiconductor material, and the second type semiconductor layer is formed of the other one of the N-type semiconductor material and the P-type semiconductor material.

12. The method according to claim 11, wherein the third electrode layer and the first electrode layer are formed at the same time, and the fourth electrode layer and the second electrode layer are formed at the same time.

* * * * *